United States Patent [19]

Bekkering et al.

[11] Patent Number: 4,565,543
[45] Date of Patent: Jan. 21, 1986

[54] AUTOMATIC INJECTION DEVICE

[75] Inventors: Hendrik M. Bekkering; Henricus H. M. Vulink, both of Olst, Netherlands

[73] Assignee: Duphar International Research B.V., Weesp, Netherlands

[21] Appl. No.: 544,704

[22] Filed: Oct. 24, 1983

[30] Foreign Application Priority Data

Oct. 27, 1982 [NL] Netherlands .......................... 8204142

[51] Int. Cl.⁴ .............................................. A61M 5/20
[52] U.S. Cl. .................................... 604/135; 604/244; 128/DIG. 12
[58] Field of Search ............... 604/135, 137, 136, 139, 604/218, 220, 244; 128/1.1, DIG. 12; 215/12 R

[56] References Cited

U.S. PATENT DOCUMENTS 2,221,739 11/1940 Reiter ................................... 604/135
4,014,331 3/1977 Head ............................... 604/223 X
4,031,893 6/1977 Kaplan et al. ....................... 604/136
4,178,928 12/1979 Tischlinger .......................... 604/139
4,225,049 9/1980 Inoue ................................. 215/12 R

FOREIGN PATENT DOCUMENTS 1528735 10/1978 United Kingdom .

Primary Examiner—Stephen C. Pellegrino
Attorney, Agent, or Firm—Stevens, Davis, Miller & Mosher

[57] ABSTRACT

The invention relates to an automatic injection device comprising a discharge mechanism, a cartridge holder and a cartridge which is slidably accommodated in the holder, the cartridge comprising a glass ampoule having an injection needle connected thereto. A sheath of shrinkable plastic sheet is shrunk around the ampoule entirely or for the greater part thereof.

6 Claims, 4 Drawing Figures

AUTOMATIC INJECTION DEVICE

The present invention relates to an automatic injection device comprising an assembly of a discharge mechanism, a cartridge holder and a cartridge which is slidably accomodated in the cartridge holder; the discharge mechanism comprising a sleeve which is open on one side, a plunger which is movable in the sleeve, a coil spring which acts on said plunger and tries to move same out of the open end of the sleeve outwards, a locking device which cooperates with said plunger so as to prevent undesired movement of the plunger, and, if desired, a safety device to block said locking device; the cartridge comprising a glass ampoule having an injection needle connected thereto, of which ampoule the part remote from the needle has the shape of a hollow cylinder having an entirely or substantially uniform inside diameter, in which is present a piston which can be moved by the plunger, and which ampoule includes an injection liquid or various injection liquids separated from each other by stoppers.

Such an injection device, namely for one injection liquid, is disclosed in British Patent Specification No. 1,528,735 in the name of applicants. The device described in said patent specification moreover comprises a spacer element between the plunger and the piston with which the content of the ampoule can be reduced at will, and a needle guard of a flexible material which keeps the needle sterile during storage of the syringe. Such a needle guard is an excellent provision and is preferably also used in the syringe according to the present invention.

Because it is usually not advisable to leave the injection liquid or, if the ampoule includes more different injection liquids, the injection liquid in the front compartment, in contact with the metal of the needle during the storage time of the syringe, the injection liquid is preferably separated from the needle by a membrane or stopper. In that case, when using the syringe, the access to needle is released when the membrane bursts due to the pressure in the ampoule or when a passage for the injection liquid is formed through or along the stopper or stoppers.

It has been found that when the device known from said British Patent Specification No. 1,528,735 is used, fracture of the glass ampoule often occurs. This can be checked by manufacturing the ampoule from glass specially hardened for this purpose. However, it is particularly difficult to harden the glass in such manner that a sufficient impact strength is reached. Therefore, glass ampoules having a sufficient impact strength are very expensive components for automatic injection devices. The force which during use of the device acts on various parts of the device, for example the ampoule, must be large because the injection needle has first to be forced into the user's body, often through the clothes, and the injection liquid has then to be injected. In order to be able to meet these requirements, a powerful coil spring must be used having a spring-power of at least approximately 120 N. In this case, however, there is a fair chance that when using the syringe the material of the ampoule cannot withstand the forces occurring upon relaxation of the spring, as a result of which fracture of the glass ampoule frequently occurs when unhardened glass is used.

In the case of fracture of the glass ampoule, the injection liquid usually leaks away out of the ampoule before it can be injected, so that the automatic injector fails at the critical instant.

It is the object of the present invention to provide an automatic injection device which does not exhibit the above-mentioned disadvantage.

This object can be achieved by means of an automatic injection device of the kind described in the opening paragraph which comprises a sheath of a shrinkable plastic sheet which is shrunk around the ampoule so that the ampoule in the longitudinal direction entirely or for the greater part is covered by the sheath of shrinkable sheet. Such a sheath for enveloping a part of the ampoule of a disposable syringe, albeit with a different purpose, is known from the non-pre-published Netherlands Patent Application No. 8103476 in the name of Applicants. The sheath is manufactured from a known plastic sheet which as a result of heating can shrink in at least one (axial) direction, for example, a prestretched sheet of PVC.

It has surprisingly been found that when such a sheath of shrinkable sheet is used, the possibility of fracture of the ampoule is reduced in such manner that an ampoule of unhardened glass may be used without any objection. This was not to be expected at all, because the wall thickness of the ampoule hardly increases as a result of the use of a sheath of shrinkable sheet: the glass wall of an ampoule commonly used for automatic injection devices is approximately 0.9 mm thick (tolerance 0.06 mm); the wall thickness of the shrunk sheet is approximately 0.06 mm.

During the assembly process of the injector, the sheath of shrinkable sheet can very simply be slid around the ampoule and be shrunk around the ampoule as described in the above-mentioned Netherlands Patent Application No. 8103476.

According to another aspect of the present invention, the risk of fracture of the glass ampoule can be even further reduced by providing the syringe with an annular member of a slightly resilient material which is provided on the open end of the ampoule remote from the needle. Such a provision can also be used very simply and hence cheaply. The annular member, preferably of a synthetic resin, for example, polypropylene, can simply be provided on the rear edge of the open ampoule during assembly of the syringe, after which the sheath of shrinkable sheet is preferably shrunk around both the ampoule and the annular member. The annular member may also be used alone, hence without the sheath of shrinkable sheet, namely between the sleeve of the firing mechanism comprising the spring and the plunger, and the end of the ampoule remote from the needle. A considerable improvement is also achieved in this case, preferably, however, the annular member is used together with the sheath of shrinkable sheet, because as a result of this combination the possibility of fracture of ampoules manufactured from unhardened glass can be minimized.

In order to prevent movement of the annular member during assembly or during storage of the syringe, the annular member is preferably constructed so as to have approximately the same outside diameter as the ampoule, a slightly smaller inside diameter than the end of the ampoule remote from the needle, and a neck fitting within said end of the ampoule.

Alternatively, the above sheath of shrinkable sheet may be shrunk not only around the ampoule body but also inwardly around the rear edge of the ampoule, thus covering said rear edge completely. This provision has proved to substantially prevent fracture of the glass ampoules, even in the absence of the above annular member, and thus forms a preferred provision in view of the cost-price of the device.

The injector described in the above-mentioned British Patent Specification No. 1,528,735 comprises a plunger which consists of a head facing the piston and forming on the rear side of an abutment for the coil spring, a central part having a uniform circumference around which the coil spring fits, and a furcated end part of reduced circumference remote from the piston and the resilient prongs or detent arms of which cooperate with the locking device. According to still another aspect of the present invention, the risk of fracture of the glass ampoule when using an automatic injection device comprising such a plunger can be even further reduced by providing around the end part of the plunger a sleeve which is open at each end and has an outside diameter which is approximately equal to that of the central part of the plunger. The sleeve is manufactured from form-retaining material, for example, a suitable synthetic resin or, preferably, metal. The above-mentioned prongs of the plunger must be sufficiently resilient to enable both the assembly in the locking device and the activation of the syringe. Therefore, the prongs are comparatively narrow so that the end part of the plunger has a smaller circumference than the central part. It has now been found that by providing a sleeve around said end part, the possiblity of fracture of the ampoule is further reduced. Such a sleeve may be used together with one of the two or with both above-mentioned provisions in order to reach the desired improvement of the automatic injector.

The above-mentioned provisions to reduce the possibility of fracture of the glass ampoule of an automatic injector are meant in particular for an automatic injection device whose ampoule is manufactured from unhardened glass. When the glass has been subjected to a special hardening, the possibility of fracture is comparatively small. However, such a hardening method, as already stated hereinbefore, is particularly complicated and hence very expensive.

BRIEF DESCRIPTION OF THE DRAWINGS

The present invention will now be described in greater detail with reference to a preferred embodiment which is shown in the drawing, in which.

Figure 1:
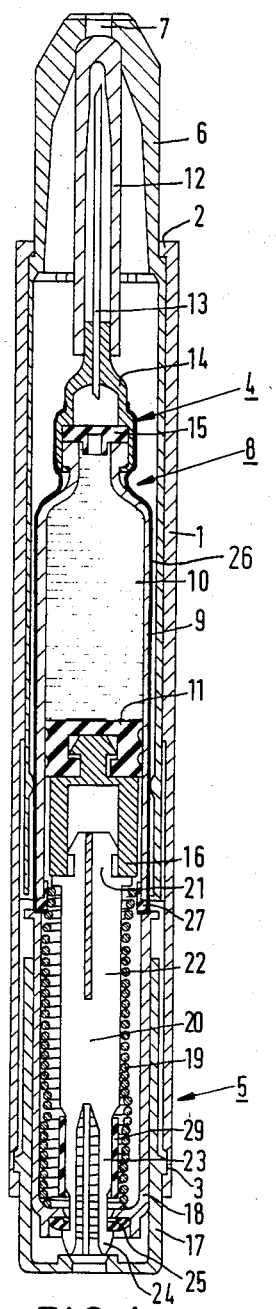
FIG. 1 is a longitudinal sectional view of a injector according to the invention.

In broad outline, the device shown in FIG. 1 does not differ from that described and shown in the British Patent Specification No. 1,528,735 mentioned before.

The embodiment shown in FIG. 1 is only one embodiment of an automatic injection device in which the provisions to reduce the possibility of fracture of the glass ampoule can advantageously be used. Other suitable examples of injectors are described and shown in non-pre-published Netherlands Patent Application No. 8103744 in the name of Applicants.

The injector shown in FIG. 1 comprises an outer sleeve 1 having inwardly bent edge 2 and circumferential groove 3 in which a cartridge assembly 4 and a discharge mechanism 5 are accomodated. The cartridge assembly comprises a cartridge holder 6 which fits in the outer sleeve and on its front end has a circular aperture 7, and a cartridge 8 which is movable in the cartridge holder. The cartridge comprises an ampoule 9 with injection liquid 10, a piston 11 at one end and a needle 13 having a needle guard 12 at the other end, said needle being connected to the ampoule by means of a needle holder 14. A membrane 15 is provided between the neck of the ampoule and the needle holder and, during storage of the syringe, keeps the injection liquid separated from the needle but, during use of the syringe, bursts open so that the injection liquid can reach the needle cannula. Finally, a spacer element 16 is provided behind the piston with which the volume of the ampoule for the injection liquid has been reduced.

As in the injector described in British Patent Specification No. 1,528,735, the discharge mechanism comprises an outer gun sleeve 17 locked (at 3) in the outer sleeve 1, an inner gun sleeve 18 slidably accomodated in the outer gun sleeve and comprising a coil spring 19. The coil spring fits around a plunger 20 with a sufficient amount of play, the plunger consisting of a plunger head 21 which is inserted in the spacer element, a central part 22 having a uniform circumference, and an end part 23 of reduced circumference. The end part consists of four resilient prongs or detent arms the conical ends 24 of which bear on a metal sealing ring 25 around an aperture in the rear face of the inner gun sleeve. In the syringe shown in FIG. 1, the safety member consisting of a cap having a safety pin which may extend between the prongs of the plunger, has already been removed so that the syringe is ready for use.

A sheath 26 of PVC shrinkable sheet is shrunk around the whole ampoule, including the neck.

Figure 2:
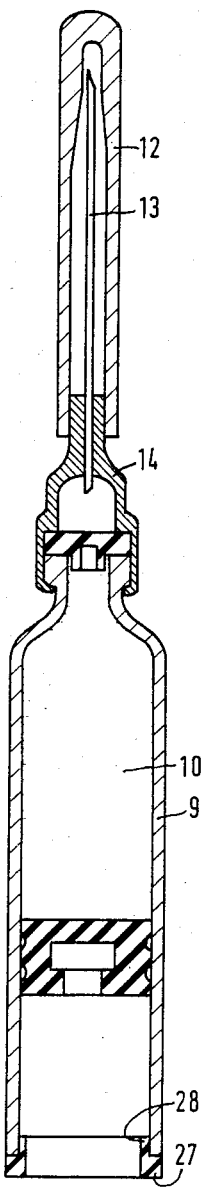
FIG. 2 is a longitudinal sectional view of a cartridge having an ampoule on the open end of which the annular member has been provided.

An annular member 27 of polypropylene is provided on the rear edge of the ampoule. This is shown more clearly in FIG. 2 in which the cartridge with the ampoule 9 and the annular member 27 are illustrated on a slightly larger scale. The annular member comprises a neck 28 which fits within the rear edge of the ampoule.

Figure 3:
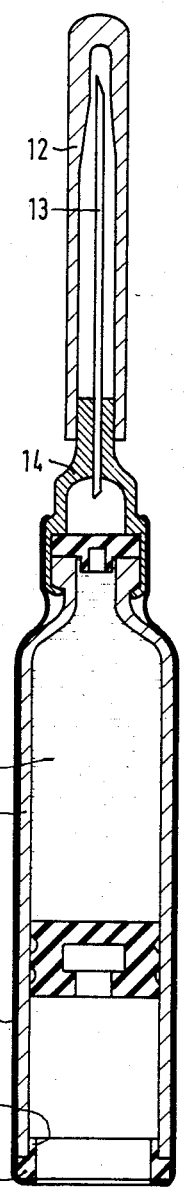
FIG. 3 shows the same cartridge, this time provided with an annular member and a sheath of shrinkable sheet.

FIG. 3 shows the same cartridge, this time provided with annular member 27 and sheath of shrinkable sheet 26. The latter is shrunk around the ampoule 9, a part of the needle holder 14 and the annular member 27. As a result of this the annular member remains located during assembly of the injector. Furthermore, around the resilient prongs of the plunger (FIG. 1) is present a metal sleeve 29 which is open at each end and the outside diameter of which is approximately equal to the diameter of the central part 22 of the plunger.

Figure 4:
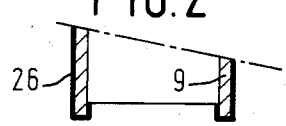
FIG. 4 shows the rear end of the ampoule, provided with a sheath of shrinkable sheet only.

In the embodiment of FIG. 4, showing the rear end of the ampoule, the annular member is not present. The sheath of shrinkable sheet 26 completely envelopes the rear edge of the ampoule 9.

It will be obvious that it is not necessary for all provisions to be present collectively, as is shown in the FIG. 1 embodiment. The sheath of shrinkable sheet may also be used advantageously alone (FIG. 4), or together with the annular member (FIG. 3), or together with the sleeve; and the annular member may be used alone (FIG. 2) or together with the sleeve. These embodiments are clear without further explanation therefore not all of them have been illustrated by means of Figures.

The use of the injector according to the present invention is the same as that of the one described in the above-mentioned British Patent Specification No. 1,528,735 and need no further explanation.

Injectors according to the present invention in which the ampoule had been manufactured from unhardened glass, were compared in their application with identical injectors without the provisions described and with the same injectors having ampoules of hardened glass. The following results were obtained.

| Provision | Injector glass ampoule | Number of tested inj. | Well emptied number | % |
|---|---|---|---|---|
| sheath of shrinkable sheet | unhardened | 200 | 198 | 99.0 |
| Annular member | unhardened | 200 | 187 | 93.5 |
| sheath plus annular member | unhardened | 200 | 200 | 100 |
| None | unhardened | 200 | 169 | 84.5 |
| None | hardened | 300 | 298 | 99.3 |

"Well emptied" is to be understood to mean herein that during use of the injector the syringe liquid has left the injector through the injection needle and has not leaked away prematurely as a result of fracture of the ampoule. In the comparative experiments reported on in the above table, the sheath of shrinkable sheet was not shrunk around the rear edge of the ampoule. When the sheath was also completely shrunk around the rear edge of the ampoule (as in FIG. 4), of the 50 glass ampoules tested, a number of 50 (100%) was well emptied. From the above results it is apparent that the percentage of fractured ampoules of unhardened glass can be reduced considerably by means of the provisions as indicated, and that by a correct choice of the provisions at least an equally great reliability can be achieved as in identical injectors having ampoules of hardened glass.

Although the preceding disclosure illustrating the ampoule as containing only one injection liquid, the ampoule may contain various injection liquids separated from each other by stoppers.

We claim:

1. An automatic injection device, comprising an assembly of a discharge mechanism, a cartridge holder and a cartridge slidably accommodated in the cartridge holder; the discharge mechanism comprising a sleeve that is open on one side, a plunger that is movable in the sleeve, a coil spring that acts on said plunger to move same toward the open end of the sleeve, a locking device that cooperates with said plunger to prevent undesired movement of the plunger; the cartridge comprising a glass ampoule having a needle connected to one end thereof and being open-ended at the opposite end thereof, a part of said ampoule remote from the needle comprising a hollow cylinder having an entirely or substantially uniform inside diameter, a piston adapted for movement by the plunger being provided in said cylinder, a movable inner sleeve surrounding said coil spring and adapted to bear against said ampoule at its open end; said syringe being characterized in that the ampoule contains at least one injection liquid; said syringe being further characterized in that an annular member of slightly resilient material is interposed between the open end of the ampoule remote from the needle and said movable inner sleeve.

2. An injection device as claimed in claim 1, wherein the annular member has approximately the same outside diameter as the ampoule, has a slightly smaller inside diameter than the end of the ampoule remote from the needle, and includes a neck portion that fits within the end of the ampoule remote from the needle.

3. An injection device as claimed in claim 1, wherein the plunger comprises a head facing the piston and forming on the rear side an abutment for the coil spring; a central part of uniform circumference around which the spiral spring fits; and a furcated end part of reduced circumference remote from the piston, said syringe being characterized in that a sleeve that is open at each end is provided around the end part, the outside diameter of said sleeve being approximately equal to that of the central part of the plunger.

4. An injection device as claimed in claim 2, wherein the plunger comprises a head facing the piston and forming on the rear side an abutment for the coil spring; a central part of uniform circumference around which the spiral spring fits; and a furcated end part of reduced circumference remote from the piston, said syringe being characterized in that a sleeve that is open at each end is provided around the end part, the outside diameter of said sleeve being approximately equal to that of the central part of the plunger.

5. An injection device as claimed in claim 1, characterized in that said ampoule contains various injection liquids separated from each other by at least one stopper.

6. An injection device as claimed in claim 1, said syringe being further characterized in that a sheath of plastic sheet is shrunk around said annular member and said ampoule entirely or for the greater part thereof.

* * * * *